US00PP28185P3

(12) United States Plant Patent
Danziger

(10) Patent No.: US PP28,185 P3
(45) Date of Patent: Jul. 11, 2017

(54) ***PHLOX* PLANT NAMED 'DPHLOX866'**

(50) Latin Name: *Phlox drummondii*
Varietal Denomination: DPHLOX866

(71) Applicant: Gavriel Danziger, Moshav Mishmar Hashiva (IL)

(72) Inventor: Gavriel Danziger, Moshav Mishmar Hashiva (IL)

(73) Assignee: Danziger "DAN" Flower Farm, Moshav Mishmar Hashiva (IL)

( * ) Notice: Subject to any disclaimer, the term of this patent is extended or adjusted under 35 U.S.C. 154(b) by 0 days.

(21) Appl. No.: 14/756,436

(22) Filed: Sep. 4, 2015

(65) Prior Publication Data

US 2017/0071101 P1 Mar. 9, 2017

(51) Int. Cl.
*A01H 5/02* (2006.01)

(52) U.S. Cl.
USPC ..... Plt./320

(58) Field of Classification Search
USPC ..... Plt./320
See application file for complete search history.

(56) References Cited

PUBLICATIONS

PLUTO Plant Variety Database Aug. 10, 2016. p. 1.*

* cited by examiner

*Primary Examiner* — Annette Para
(74) *Attorney, Agent, or Firm* — C. A. Whealy

(57) ABSTRACT

A new and distinct cultivar of *Phlox* plant named 'DPHLOX866', characterized by its upright to outwardly spreading and uniformly mounding plant habit; moderately vigorous growth habit; freely branching habit; dense and full appearance; freely flowering habit; long flowering period; white-colored flowers; and relative tolerance to high temperatures.

2 Drawing Sheets

Botanical designation: *Phlox drummondii.*
Cultivar denomination: 'DPHLOX866'.

BACKGROUND OF THE INVENTION

The present invention relates to a new and distinct cultivar of *Phlox* plant, botanically known as *Phlox drummondii* and hereinafter referred to by the name 'DPHLOX866'.

The new *Phlox* plant is a product of a planned breeding program conducted by the Inventor in Moshav Mishmar Hashiva, Israel. The objective of the breeding program is to create new mounding and full *Phlox* plants with numerous attractive flowers and low sensitivity to Powdery Mildew.

The new *Phlox* plant originated from an open-pollination in Moshav Mishmar Hashiva, Israel in October, 2011 of a proprietary selection of *Phlox drummondii* identified as code number PH-9-1112, not patented, as the female, or seed, parent with an unknown selection of *Phlox drummondii* as the male, or pollen, parent. The new *Phlox* plant was discovered and selected by the Inventor as a single flowering plant within the progeny of the stated open-pollination in a controlled greenhouse environment in Moshav Mishmar Hashiva, Israel in April, 2012.

Asexual reproduction of the new *Phlox* plant by vegetative terminal cuttings in a controlled greenhouse environment in Moshav Mishmar Hashiva, Israel since July, 2012 has shown that the unique features of this new *Phlox* plant are stable and reproduced true to type in successive generations.

SUMMARY OF THE INVENTION

Plants of the new *Phlox* plant have not been observed under all possible combinations of environmental and cultural conditions. The phenotype may vary somewhat with variations in environmental conditions such as temperature and light intensity without, however, any variance in genotype.

The following traits have been repeatedly observed and are determined to be the unique characteristics of 'DPHLOX866'. These characteristics in combination distinguish 'DPHLOX866' as a new and distinct *Phlox* plant:

1. Upright to outwardly spreading and uniformly mounding plant habit.
2. Moderately vigorous growth habit.
3. Freely branching habit; dense and full appearance.
4. Freely flowering habit; long flowering period.
5. White-colored flowers.
6. Relatively tolerant to high temperatures.

Plants of the new *Phlox* can be compared to plants of the female parent selection. Plants of the new *Phlox* differ primarily from plants of the female parent selection in the following characteristics:

1. Plants of the new *Phlox* are more outwardly spreading than plants of the female parent selection.
2. Plants of the new *Phlox* are more vigorous than plants of the female parent selection.
3. Plants of the new *Phlox* and the female parent selection differ in flower color as plants of the female parent selection have purple-colored flowers.

Plants of the new *Phlox* can be compared to plants of *Phlox drummondii* 'Power *Phlox* White', not patented. In side-by-side comparisons conducted in Moshav Mishmar Hashiva, Israel, plants of the new *Phlox* and 'Power *Phlox* White' differed in the following characteristics:

1. Plants of the new *Phlox* were more mounding than and not as loose and open as plants of 'Power *Phlox* White'.
2. Plants of the new *Phlox* had larger flowers than plants of 'Power *Phlox* White'.
3. Plants of the new *Phlox* and 'Power *Phlox* White' differed in flower color as plants of 'Power *Phlox* White' had white-colored flowers blushed with pink.

BRIEF DESCRIPTION OF THE PHOTOGRAPHS

The accompanying colored photographs illustrate the overall appearance of the new *Phlox* plant showing the colors as true as it is reasonably possible to obtain in colored reproductions of this type. Colors in the photographs may differ slightly from the color values cited in the detailed botanical description which accurately describe the colors of the new *Phlox* plant.

The photograph on the first sheet is a side perspective view of a typical flowering plant of 'DPHLOX866' grown in a container.

The photograph on the second sheet is a close-up view of typical flowers of 'DPHLOX866'.

DETAILED BOTANICAL DESCRIPTION

The aforementioned photographs and following observations, measurements and values describe plants grown during the autumn in 13-cm containers in an outdoor nursery in Moshav Mishmar Hashiva, Israel and under cultural practices typical of commercial *Phlox* production. During the production of the plants, day temperatures ranged from 18° C. to 36° C., night temperatures ranged from 10° C. to 17° C. and light levels ranged from 7,000 to 10,000 foot-candles. Plants were pinched one time and were two months old when the photographs and description were taken. Supplemental flower information was collected from plants grown in 22-cm containers during the summer in an outdoor nursery in Loudon, N.H. and under cultural practices typical of commercial Diascia production. During the production of these plants, day temperatures averaged 27° C., night temperatures averaged 13° C. and maximum light levels were 10,000 foot-candles. These plants were pinched one time and were 17 weeks old when the supplemental flower information was taken. In the following description, color references are made to The Royal Horticultural Society Colour Chart, 2007 Edition, except where general terms of ordinary dictionary significance are used.

Botanical classification: *Phlox drummondii* 'DPHLOX866'.

Parentage:

*Female, or seed, parent*.—Proprietary selection of *Phlox drummondii* identified as code number PH-9-1112, not patented.

*Male, or pollen, parent*.—Unknown selection of *Phlox drummondii*, not patented.

Propagation:

*Type*.—By terminal vegetative cuttings.

*Time to initiate roots, summer*.—About five to six days at temperatures about 20° C.

*Time to initiate roots, winter*.—About seven to eight days at temperatures ranging from 14° to 18° C.

*Time to produce a rooted young plant, summer*.—About three weeks at temperatures ranging from 25° to 35° C.

*Time to produce a rooted young plant, winter*.—About four weeks at temperatures ranging from 14° to 20° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Herbaceous annual plant; upright to outwardly spreading and uniformly mounding plant habit; broad inverted triangle; moderately vigorous growth habit; freely branching habit with about eleven primary laterals developing per plant, each primary lateral with numerous secondary laterals; dense and bushy appearance.

*Plant height*.—About 15 cm.

*Plant width* (*spread*).—About 14 cm.

*Lateral branches*.—Length: About 12 cm. Diameter: About 2.5 mm. Internode length: About 2 cm to 3 cm. Strength: Strong. Aspect: About 45° to 80° from vertical. Texture: Pubescent. Color: Close to 146D.

Leaf description:

*Arrangement*.—Opposite, simple; sessile.

*Length*.—About 4 cm to 5 cm.

*Width*.—About 1.5 cm.

*Shape*.—Oblong.

*Apex*.—Acute.

*Base*.—Rounded, clasping.

*Margin*.—Entire.

*Texture, upper and lower surfaces*.—Pubescent.

*Venation pattern*.—Pinnate.

*Color*.—Developing and fully expanded leaves, upper surface: Close to 146B; venation, close to 146B. Developing and fully expanded leaves, lower surface: Close to 146C; venation, close to 146C.

Flower description:

*Flower type and flowering habit*.—Single rotate salverform flowers arranged in small panicles; flowers face mostly upright to outwardly; freely flowering habit with about four to eight flowers per inflorescence and about 100 flowers per plant.

*Fragrance*.—None detected.

*Natural flowering season*.—Long flowering season, plants flower continuously from spring until frost in Israel.

*Postproduction longevity*.—Flowers last about four days on the plant; flowers not persistent.

*Flower buds*.—Height: About 1.2 cm to 1.5 cm. Diameter: About 2.5 mm to 3 mm. Shape: Obovate. Color: Close to 1D.

*Inflorescence height*.—About 3.5 cm.

*Inflorescence diameter*.—About 5 cm.

*Flower diameter*.—About 2.6 cm.

*Flower depth*.—About 1.8 cm.

*Flower throat diameter*.—About 3 mm.

*Flower tube length*.—About 1 cm.

*Flower tube diameter, at the base*.—About 4 mm.

*Petals*.—Quantity per flower and arrangement: Five petals arranged in a single whorl and fused towards the base into a narrow tube. Length from throat: About 1.2 cm. Width: About 1.1 cm. Shape: Obovate. Apex: Rounded, obtuse. Margin: Entire. Texture, petal lobes, upper and lower surfaces: Smooth, glabrous. Texture, throat: Smooth, glabrous. Texture, tube: Tomentose. Luster, petal lobes, upper and lower surfaces: Matte. Luster, throat: Satiny. Luster, tube: Satiny. Color: Developing petals, upper and lower surfaces: Close to 155C. Fully expanded petals, upper and lower surfaces: Close to 155C; color does not change with development. Throat: Close to 155C. Tube: Close to 157A.

*Sepals*.—Quantity per flower and arrangement: Five sepals arranged in a single whorl and fused towards the base into a narrow tube. Length: About 8 mm to 10 mm. Width: Less than 1 mm. Shape: Lanceolate. Apex: Acuminate to apiculate. Margin: Entire. Texture, upper and lower surfaces: Smooth, glabrous. Color: When developing, upper and lower surfaces: Distally, close to 146B; proximally, close to 144B. Fully opened, upper and lower surfaces: Distally, close to 146B; proximally, close to 144B.

*Peduncles*.—Length: About 1.5 cm to 2 cm. Diameter: About 2 mm. Angle: Upright to about 40° to 45° from vertical. Strength: Strong. Texture: Pubescent. Color: Close to 144B.

*Pedicels*.—Length: About 4 mm to 5 mm. Diameter: About 1 mm. Angle: About 30° from peduncle axis. Strength: Strong, flexible. Texture: Pubescent. Color: Close to 144B.

*Reproductive organs*.—Stamens: Quantity per flower: Typically five. Anther length: About 1.5 mm. Anther shape: Elliptic to narrowly oblong. Anther color: Close to 12A. Pollen amount: Moderate. Pollen color: Close to 13A. Pistils: Quantity per flower: One. Pistil length: About 4 mm. Stigma shape: Three-parted. Stigma color: Close to 155C. Style length: About 1 mm. Style color: Close to 155C. Ovary color: Close to 144A.

*Fruits*.—Length: About 3 mm. Diameter: About 3 mm. Texture: Smooth, glabrous. Color: Close to 144B.

*Seeds*.—Quantity per fruit: About two. Length: About 2.2 mm. Diameter: About 1.9 mm. Texture: Smooth, glabrous. Color: Close to 200C.

Disease & pest resistance: Plants of the new *Phlox* have not been noted to be resistant to pathogens and pests common to *Phlox* plants.

Temperature tolerance: Plants of the new *Phlox* have been observed to tolerate temperatures ranging from about 5° C. to about 40° C.

It is claimed:

1. A new and distinct *Phlox* plant named 'DPHLOX866' as illustrated and described.

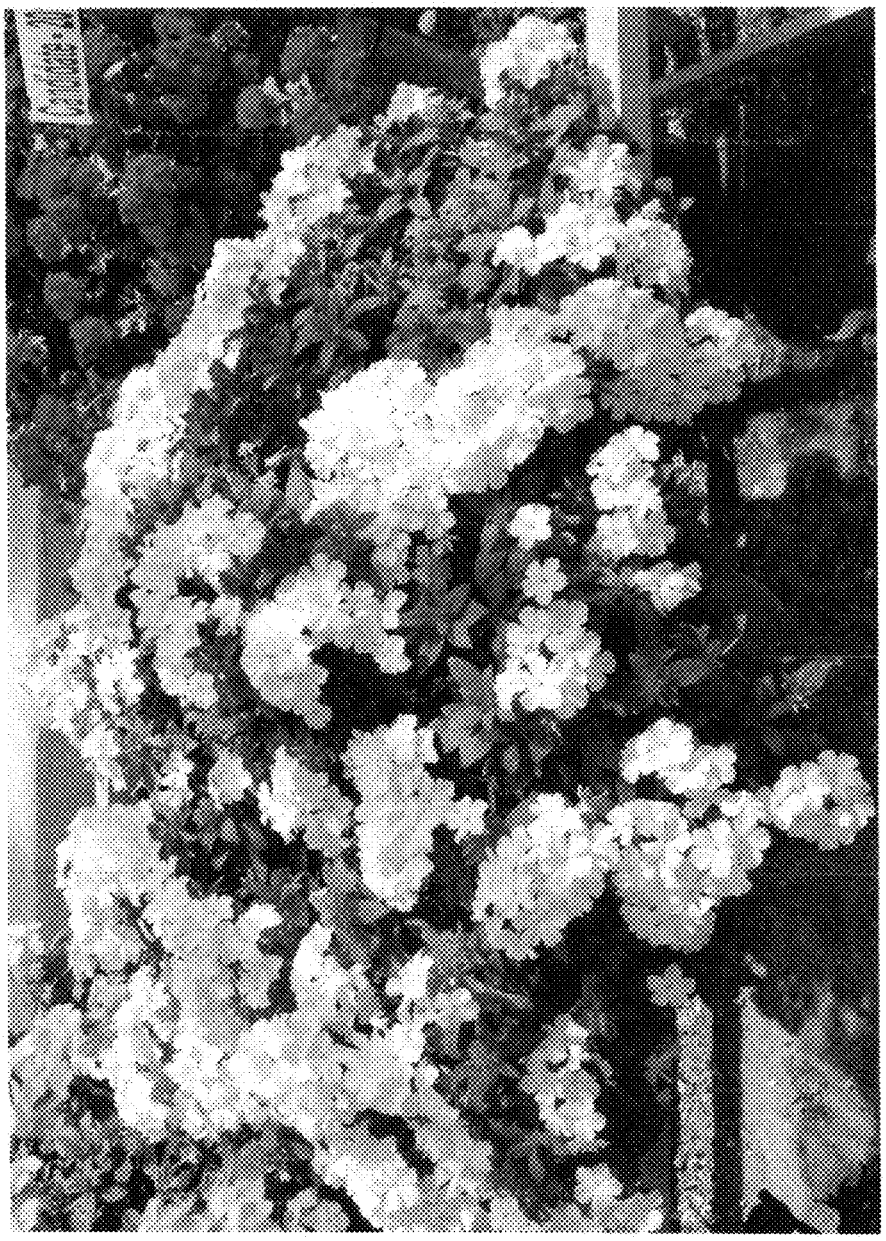

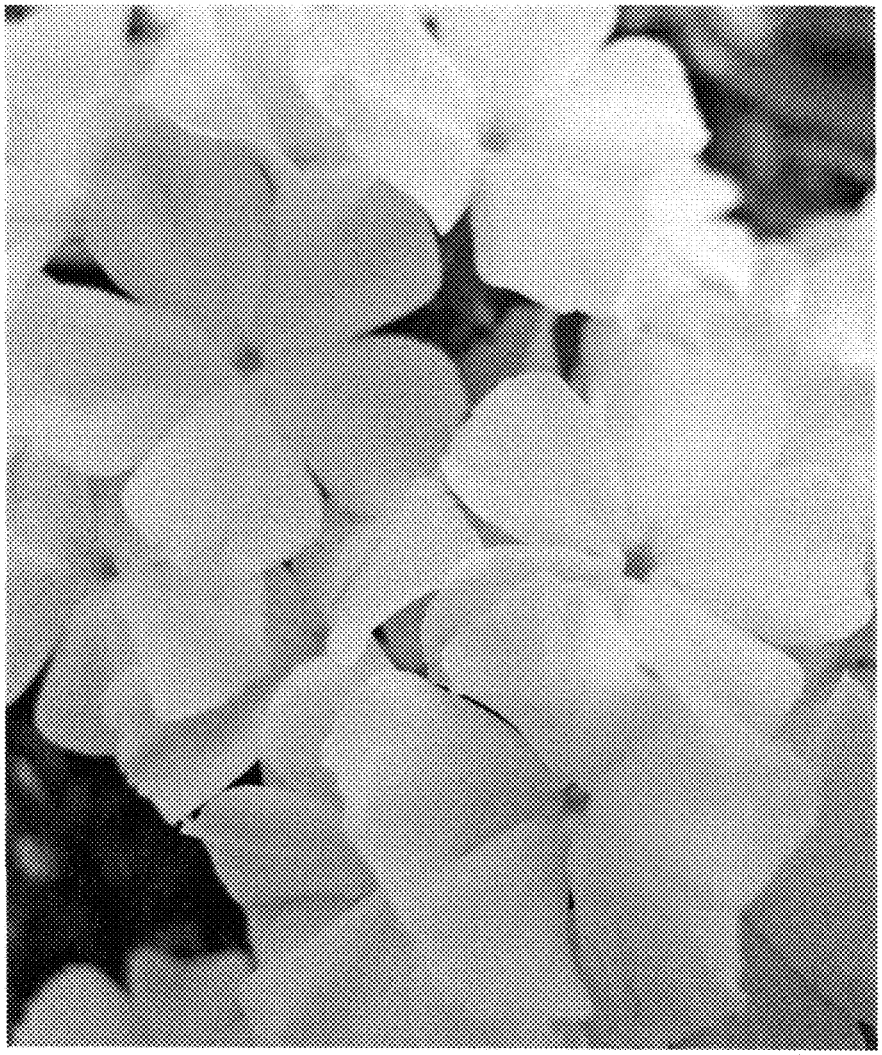

* * * * *